United States Patent
Jaladi et al.

(10) Patent No.: US 11,392,669 B1
(45) Date of Patent: Jul. 19, 2022

(54) MESSAGE TRANSMITTAL IN ELECTRONIC PRIOR AUTHORIZATION REQUESTS

(71) Applicant: Allscripts Software, LLC, Raleigh, NC (US)

(72) Inventors: Venkata Naga Bhaskar Rao Jaladi, Bangalore (IN); Nikhil Joshi, Pune (IN); Sreemanta Dash, Bangalore (IN)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 608 days.

(21) Appl. No.: 15/231,658

(22) Filed: Aug. 8, 2016

(51) Int. Cl.
*G16H 10/60* (2018.01)
*G06F 19/00* (2018.01)

(52) U.S. Cl.
CPC ...... *G06F 19/3456* (2013.01); *G06F 19/3418* (2013.01); *G16H 10/60* (2018.01)

(58) Field of Classification Search
CPC ............... G16H 20/10; G16H 19/3481; G06F 19/3456; G06F 19/328; G06Q 50/24
See application file for complete search history.

(56) References Cited

U.S. PATENT DOCUMENTS

| | | | | |
|---|---|---|---|---|
| 2011/0282690 | A1* | 11/2011 | Patel | G06Q 30/0603 705/3 |
| 2013/0060575 | A1* | 3/2013 | Nee | G06Q 50/22 705/2 |
| 2016/0342752 | A1* | 11/2016 | Stueckemann | G06F 19/328 |

* cited by examiner

*Primary Examiner* — Jason S Tiedeman
*Assistant Examiner* — Emily Huynh
(74) *Attorney, Agent, or Firm* — Calfee, Halter & Griswold LLP

(57) ABSTRACT

A server computing device executing an electronic health records (EHR) receives an indication from a client computing device that approval from a pharmacy benefits manager (PBM) with respect to prescribing a medication and/or treatment to a patient is requested. The EHR causes the server computing device to transmit an approval request to a computing system of the PBM, and monitors incoming messages for an approval message from the PBM. When the approval message is received, the ERR constructs a prescription for the medication and/or treatment for the patient and causes the prescription to be transmitted to a pharmacy.

20 Claims, 7 Drawing Sheets

MESSAGE TRANSMITTAL IN ELECTRONIC PRIOR AUTHORIZATION REQUESTS

BACKGROUND

For some patients, some types of medication, and/or some treatments, a pharmacy benefits manager (PBM) must approve a medication and/or treatment for a patient prior to a clinician prescribing the medication and/or treatment to the patient. This is referred to as "pre-approval." The conventional workflow for the pre-approval process is as follows: 1) the clinician has an encounter with the patient, where the clinician determines that a medication and/or treatment should be prescribed to the patient; 2) the clinician ascertains that the PBM must approve the medication and/or treatment for the patient prior to the clinician writing a prescription; 3) the clinician causes an approval request to be delivered to the PBM; 4) the PBM reviews the approval request; 5) oftentimes, the PMB requests additional information from the clinician, where the additional information can include clarification about the patient, the medication and/or the treatment, documentation about the patient, medication, and/or treatment, and so forth. There is often a significant delay between when the clinician submits the approval request and when the PBM requests additional information from the clinician; 6) the clinician generates a response to the request for information and provides the response to the PBM. Generating the response may require contacting the patient, which may be burdensome, as the patient encounter may have been completed and the patient may have left a facility between the time that the approval request was generated and submitted to the PBM and the time when the PBM requested additional information; 7) once the PBM receives the response to the request for additional information, the PBM determines whether or not to approve the approval request; 8) when the PBM approves the approval request, the PBM provides an approval message to the clinician; 9) when the clinician receives the approval message, the clinician writes the prescription and provides the subscription to a pharmacy that fills the prescription for the patient.

This process is particularly burdensome on the clinician. Rather than focusing on providing optimal care for the patient, the clinician must spend time gathering requested information, waiting for communications from the PBM, and so forth. This may incentivize the clinician to avoid prescribing medications and/or treatments that require pre-approval from a PBM, even when the clinician believes that the medication and/or treatment is in the best interests of the patient.

Electronic health record applications (EHRs) have been configured with functionality that is directed towards reducing some of this burden on the clinician when prescribing medication and/or treatment that requires pre-approval from a PBM. For example, an EHR can be configured with functionality that allows for the clinician to communicate electronically with the PBM and/or the pharmacy. In an example, when the clinician is using the EHR while providing care to the patient, the clinician can be immediately informed that prescribing a medication and/or treatment for the patient requires pre-approval from a PBM. Responsive to receipt of input from the clinician that the clinician wishes to prescribe the medication and/or treatment to the patient, the EHR can cause the approval request to be transmitted to a computing system of the PBM. Further, the request for additional information (mentioned above) can be delivered to the EHR, which can cause the request for information to be presented on a display of a computing device operated by the clinician. The clinician may respond to the request for additional information using the EHR, which in turn can transmit the clinician response back to the PBM computing system. The EHR can further be configured to inform the clinician of when the PBM has approved (or not approved) the approval request. Responsive to receiving this message, the clinician may then write the prescription for the medication and/or treatment for the patient.

While the conventional EHR eases the burden on the clinician with respect to the above described pre-approval process by providing a centralized mechanism for communicating with the PBM, the process remains arduous for the clinician, as the clinician must interact with the EHR with respect to prescribing medication to the patient three separate times: first when generating the approval request; secondly when responding to a request for additional information from the PBM, and thirdly to monitor the EHR for a response from the PBM. Accordingly, this workflow, as noted above, may lead to clinicians avoiding prescribing medication and/or treatment to their patients, where such medication and/or treatment requires pre-approval of the PBM.

SUMMARY

The following is a brief summary of subject matter that is described in greater detail herein. This summary is not intended to be limiting as to the scope of the claims.

Described herein are various technologies pertaining to a computer-executable EHR, wherein the EHR is configured to improve the efficiency of an electronic prescription process when approval from a PBM is required prior to a clinician prescribing a medication and/or treatment to a patient of the clinician. More specifically, the EHR is configured to reduce a number of times that the clinician must interact with the EHR, compared with conventional EHRs, when pre-approval is required for prescribing medication and/or treatment for a patient by way of the EHR.

In operation, a client computing device (such as a tablet computing device, a mobile telephone, a desktop computing device, etc.) is operated by a clinician who is providing care to a patient. The client computing device has an application (client application) executing thereon that interfaces with an EHR executing on a server computing device that is in network communication with the client computing device. The client application may be an application dedicated to the EHR, a web browser, or the like. The client computing device is employed by the clinician to identify the patient, a medication or treatment that is to be prescribed to the patient, an identity of a pharmacy that is to fill a prescription for the medication and/or treatment, and a mode in which the pharmacy is to receive the prescription (e.g. by way of a printer at the pharmacy, by way of an electronic facsimile, by way of an e-prescription system, etc.). The client computing device transmits this information to a server computing device that is executing the EHR, where the information is transmitted by way of a suitable network connection (such as an intranet). The EHR receives and stores the information, and further generates an approval request (which may also be referred to as an "authorization request") based upon such information. The approval request can include an identifier of the patient and an identifier of a medication and/or treatment that is to be prescribed to the patient. The EHR then causes the server computing device to transmit the approval request, where the approval request is directed towards a PBM computing system (e.g. a computing system operated by the PBM).

An employee of the PBM can review the approval request and may request additional information from the clinician. The PBM computing system transmits an information request, which is received at the server computing device that executes the EHR. When the clinician is in an authenticated session with the EHR (e.g., the clinician has provided authentication information to the EHR by way of the client application within some time range from a current time), the EHR can transmit the request for information to the client computing device operated by the clinician. The client computing device receives requested information from the clinician, and upon receipt of a command from the clinician at the client computing device, the client computing device transmits the response to the request for information to the server computing device that executes the EHR. The server computing device, in turn, transmits the response, where the response is directed to the PBM computing system.

The employee of the PBM (or another employee) reviews the response and, for example, can approve the request to prescribe the medication and/or treatment to the patient. The PBM computing system, in response to receipt of input from the PBM employee, generates and transmits an approval message, which is directed towards the EHR. The approval message, for example, can include an approval code.

The server computing device receives the approval message, wherein the EHR executing on the server computing device is configured to monitor incoming messages for approval messages. When the EHR ascertains that the approval message has been received, the EHR can compare content of the approval message with stored information pertaining to pending approval requests. In this example, the EHR can determine that the above-mentioned request has been approved by the PBM. In response to determining that the request has been approved by the PBM, the EHR can construct a prescription for the medication and/or treatment for the patient identified in the approval request. For instance, the prescription can be constructed based upon the identity of the pharmacy indicated in the approval request, as well as the mode of communication identified in the approval request. Responsive to constructing the prescription, the EHR can cause the server computing device to transmit the prescription to a device of the pharmacy in accordance with the communication mode previously identified by the clinician. It can be ascertained that the construction of the prescription and the transmittal of the prescription to the device of the pharmacy can be undertaken without any additional input from the client computing device operated by the clinician. Hence, the clinician need not monitor the client computing device for a notification that the approval request has been approved by the PBM for a prescription for the patient to be generated and filled by the pharmacy.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
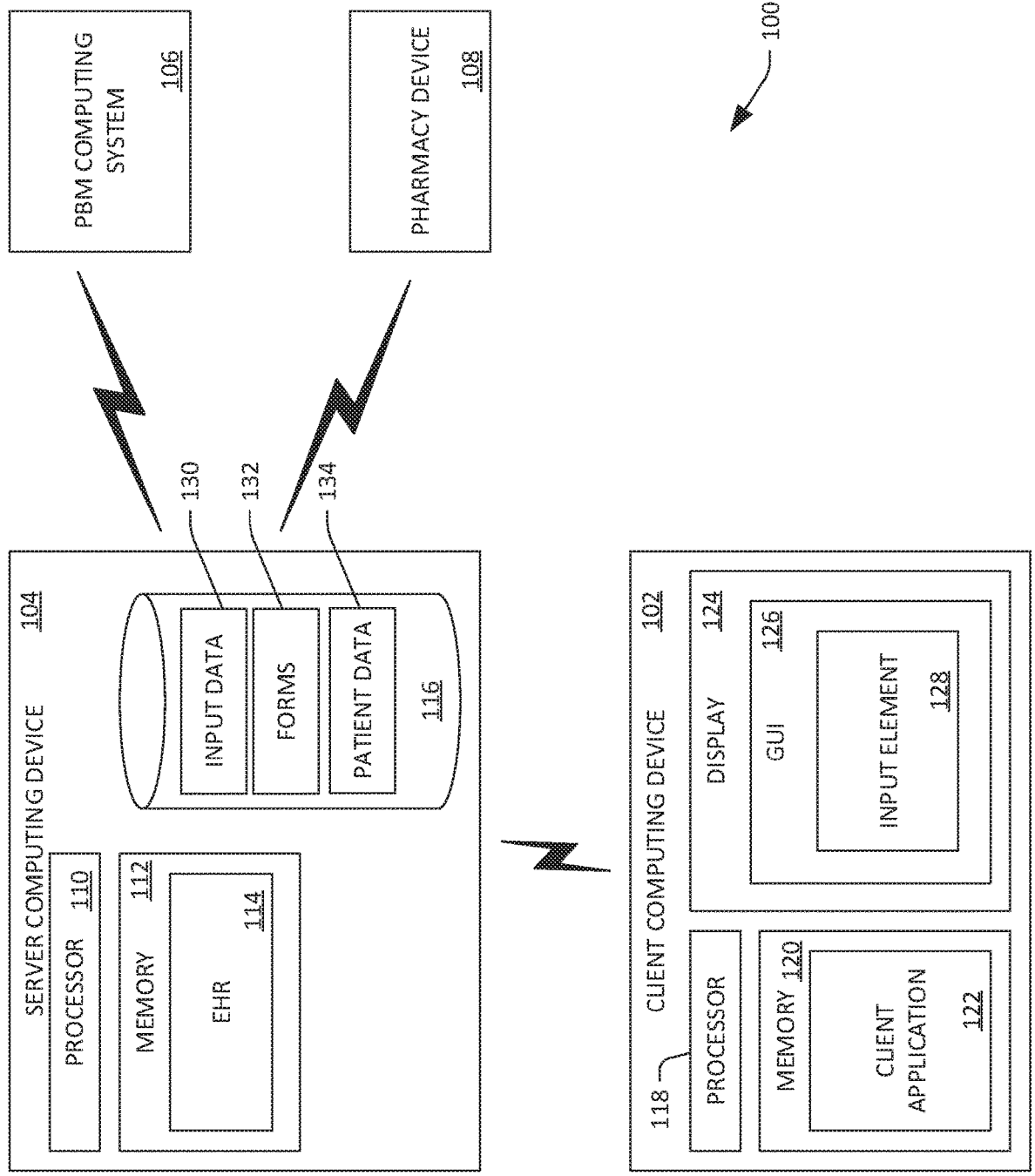
FIG. 1 is a functional block diagram of an exemplary computing system that is configured to automatically generate and transmit a prescription to a pharmacy device responsive to receipt of an approval message generated by a PBM computing system.

Various technologies pertaining to electronic communications transmitted between computing systems when pre-approval with respect to a patient, medication, and/or treatment is required are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

With reference now to FIG. 1, an exemplary computing system 100 is illustrated. The exemplary computing system 100 includes a client computing device 102 that is operated by a clinician in a healthcare environment. The client computing device 102 may be any suitable type of computing device including, but not limited to, a laptop computing device, a tablet computing device, a mobile telephone, a wearable computing device (e.g., a watch, eyewear, etc.), a kiosk, etc. The system 100 further includes a server computing device 104 that is in network communication with the client computing device 102. For example, the server computing device 104 and the client computing device 102 can be co-located in a healthcare facility. In another example, the server computing device 104 may be remotely located from the client computing device 102 (e.g., the server computing device 104 may be "in the cloud").

The computing system 100 also includes a pharmacy benefits manager (PBM) computing system 106, which can be or include a computing device operated by an employee of the PBM, a server computing device operated by the PBM, etc. The PBM computing system 106 is in network communication with the server computing device 104 (e.g., by way of the Internet, a secure network channel, etc.). The system 100 also includes a pharmacy device 108 that can be located at a pharmacy. The pharmacy device 108 may be a fax machine, a computing device, kiosk, a printer, or the like. The pharmacy device 108 is in communication with the server computing device 104 by way of a network connection.

The server computing device 104 includes a processor 110 and memory 112. The memory 112 has an electronic health record application (EHR) 114 loaded therein, wherein the EHR 114 is executed by the processor 110. The server computing device 104 also includes a data store 116 that stores data relating to healthcare workers, patients, PBMs, etc. The client computing device 102 includes a processor 118 and memory 120, wherein a client application 122 is loaded in the memory 120 and executed by the processor 118. The client application 122, when executed by the processor 118, is configured to interface with the EHR 114 executing on the server computing device 104. For instance, the client application 122 may be dedicated to the EHR 114. In another example, the client application 122 may be a browser, which can retrieve computer-executable instructions and data from the EHR 114 executing on the server computing device 104. The client application 122 is configured to transmit data to the EHR 114 and retrieve data from the EHR 114 for presentation to the clinician.

The client computing device 102 also includes a display 124, wherein a graphical user interface (GUI) 126 corresponding to the EHR 114 (and presented by way of the client application 122) is presented on the display 124. The GUI 126 is configured to present information to the clinician about at least one patient and receive information from the clinician about the at least one patient.

The EHR 114 executing on the server computing device 104 is configured to generate a prescription and cause the prescription to be transmitted to the pharmacy device 108 more efficiently when compared to conventional EHRs. More specifically, the clinician may operate the client computing device 102 such that the client application 122 executes on the client computing device 102. As indicated previously, the client application 122 is configured to transmit data to the EHR 114 and receive data generated by the EHR 114. Thus, the clinician may set forth, for instance, authentication data to the client application 122 by way of the graphical user interface 126. This authentication data may be a username and password, biometric data (fingerprint, voice, iris scan, etc.), or the like. The client application 122 transmits the authentication data to the EHR 114, which authenticates the clinician based upon the authentication data. Responsive to authenticating the clinician, the EHR 114 can transmit data to the client computing device 102, and the client computing device 102 can present this data in the graphical user interface 126. In a non-limiting example, the data shown in the graphical user interface 126 may be about a patient to whom the clinician is providing care. The clinician, in the scope of the provision of care, can indicate a desire to prescribe a medication and/or treatment to the patient. For instance, the clinician may indicate desire to prescribe a particular medication and/or treatment to the patient by way of the graphical user interface 126. The medication and/or treatment that is to be prescribed to the patient may require approval from the PBM prior to the clinician being able to generate a prescription for the medication and/or treatment for the patient. For instance, the data store 116 may include a database that indicates which medications and/or treatments, with respect to one or more patients, require approval by one or more PBMs, and the EHR 114 can communicate information relating to pre-approval to the client computing device 102 for presentment in the GUI 126 on the display 124 to indicate to the clinician that the medication and/or treatment to be prescribed to the patient must be approved by the PBM.

The GUI 126 can include an input element 128 that can be employed by the clinician to indicate to the EHR 114 that the EHR 114 is to automatically generate and transmit a prescription responsive to the EHR 114 receiving an approval message from the PBM computing system 106. The input element 128 may initially be set to a default position, wherein the default position is that the clinician must provide input prior to the prescription being transmitted to the pharmacy device 108. In this example, however, the clinician indicates that the EHR 114 is to automatically construct and transmit a prescription for the medication and/or treatment for the patient to the pharmacy device 108.

When interacting with the client computing device 102, and when providing care to the patient, the clinician can cause the client application 122 executing on the client computing device 102 to transmit the following information for receipt by the EHR 114 executing on the server computing device 104: 1) an identity of the medication and/or treatment that is to be prescribed to the patient; 2) an identifier of a pharmacy that is to fill the resultant prescription; and 3) a mode of communication to be employed when providing the pharmacy with the prescription. For instance, by way of the graphical user interface 126, the clinician can indicate that the prescription is to be printed at the pharmacy, delivered to electronic fax of the pharmacy, provided to an electronic prescription system at the pharmacy, etc.

The client application 122 executing on the client computing device 102 causes the above-referenced information to be transmitted to the server computing device 104, where it is received by the EHR 114. The EHR 114 stores this information as at least a portion of input data 130 in the data store 116. Thus, the input data 130 can include: 1) an identifier of the clinician; 2) an identifier of the patient; 3) an identifier of the medication and/or treatment to be prescribed to the patient; 4) an identifier of a pharmacy that is to fill a resulting prescription; 5) and an identifier of a communication modality to be used when providing the pharmacy with the prescription.

Further, responsive to receipt of this information from the client computing device 102, the EHR 114 can generate an approval request (also referred to as an "authorization request") and cause the server computing device 104 to direct the approval request to the PBM computing system 106. For example, the data store 116 may include forms 132, where one of such forms may be a form acceptable to the PBM computing system 106 for providing an approval request. The EHR 114 can generate the approval request by populating appropriate fields in the selected form. The approval request can include: 1) an identifier of the clinician; 2) an identifier of the patient; 3) an identifier of the medication and/or treatment; 4) an identifier of a dosage of the medication; 5) an indication as to whether the prescription is to be refillable, etc. Further, the EHR 114 can include a reference number in the approval request, wherein all future communications pertaining to the approval request between the server computing device 104 and the PBM computing system 106 can include the reference number. The EHR 114, responsive to constructing the approval request, can cause the server computing device 104 to transmit the approval request, wherein the approval request is directed towards the PBM computing system 106.

The PBM computing system 106, responsive to receiving the approval request, can present the approval request to an employee of the PBM. Such employee can review the approval request and, for example, may request additional information about the request. For instance, the PBM may require additional documentation, may wish for clarification on why the medication and/or treatment is to be prescribed to the patient, and so forth. The PBM computing system 106 can transmit an electronic message (an information request) that is directed towards the server computing device 104 that is executing the EHR 114. The server computing device 104 can receive the information request and the EHR 114 can cause the information request to be transmitted to the client computing device 102 when the client computing device 102 is operated by the clinician (e.g., when the clinician has set forth authentication data and has been authenticated by the EHR 114). The client computing device 102 may receive input from the clinician, where the input pertains to a response to the additional information requested in the information request. For instance, the GUI 126 may include a text entry field, and the client computing device 102 can receive requested information set forth by the clinician by way of such text entry field. In another example, the clinician may cause documents to be attached to an answer to the information request.

Once the clinician believes he or she has sufficiently answered information request, the clinician can operate the client computing device 102 to cause the answers to be provided to the EHR 114, and the EHR 114, responsive to receipt of the answers, can construct an electronic message for transmittal to the PBM computing system 106. This electronic message may include answers set forth by the clinician. In an exemplary embodiment, the EHR 114 can be configured to pre-populate fields in an attempt to assist the clinician in providing the requested information. For example, the data store 116 can include patient data 134, and the EHR 114 can be configured to search the patient data 134 responsive to receipt of the information request from the PBM computing system 106. For example, the EHR 114 can perform a search over the patient data 134 based upon an identity of the patient in the information request, an identity of the clinician in the information request, an identity of the medication in the information request, and so forth. The EHR may then provide the client application 122 with proposed answers to the information request, wherein the clinician is then able to review, modify, and/or approve the answers.

An employee of the PBM may review the answers received from the server computing device 104, and, for example, based on these answers, can approve the approval request. The PBM computing system 106, responsive to receiving an indication that the PBM employee has approved the approval request, can cause an approval message to be transmitted, wherein the approval message is directed to the server computing device 104. The approval message, for example, can include the reference number noted above as well as an authorization code, which can have a format known to the EHR 114. The authorization code can indicate to the EHR 114 that the approval request identified by the reference number in the approval message has been approved. Further, the approval message can optionally include an identifier of the clinician, an identifier of the patient, an identifier of the medication, and so forth.

The server computing device 104 receives the approval message, whereupon it is received by the EHR 114. For instance, the approval message may be placed in a queue that is monitored by the EHR 114. The EHR 114 reviews the approval message and identifies the approval request by comparing content of the approval message (e.g., the reference number) with data in the input data 130, and can further ascertain that the approval request has been granted based upon the authorization code included in the approval message. Responsive to determining that the approval request has been granted, the EHR 114 can construct a prescription (automatically) for provision to the pharmacy device 108. For instance, the forms 132 can include a form that corresponds to the pharmacy and the pharmacy device 108 that is to receive the prescription. Such form can be identified based upon the input data 130 (which includes the identifier of the pharmacy and the identifier of the communication mode to be used to deliver the prescription to the pharmacy). The prescription may then be populated with information from the input data 130, such as an identifier of the medication, an identifier of the dosage, an identifier of the clinician, an identifier of the patient, the authorization code, and so forth.

The EHR 114 can then cause the prescription to be transmitted to the pharmacy device 108, whereupon the pharmacy device 108 can present the prescription to a pharmacist who can fill the prescription for the patient. It can, therefore, be ascertained that the prescription can be constructed and provided to the pharmacy device 108 without the EHR 114 transmitting a confirmation to the client computing device 102 that the approval request has been approved by the PBM, and further without requiring additional input from the clinician to construct and transmit the prescription. This further reduces the burden of the clinician who need not monitor notifications for some indefinite time period after setting forth additional information requested by the PBM. Optionally, the EHR 114 can be configured to transmit a notification to the client computing device 102 to indicate to the clinician that the prescription has been constructed and transmitted to the pharmacy device 108. The EHR 114 can further, optionally, be configured to construct and transmit a message to a computing device operated by the patient to inform the patient that the prescription has been transmitted to the pharmacy for filling. This electronic message may be an e-mail, a text message, or like. In yet another example, the EHR 114 can interface with a patient portal application and can transmit a notification that the prescription has been constructed and transmitted to the pharmacy to the patient portal application.

Figure 2:
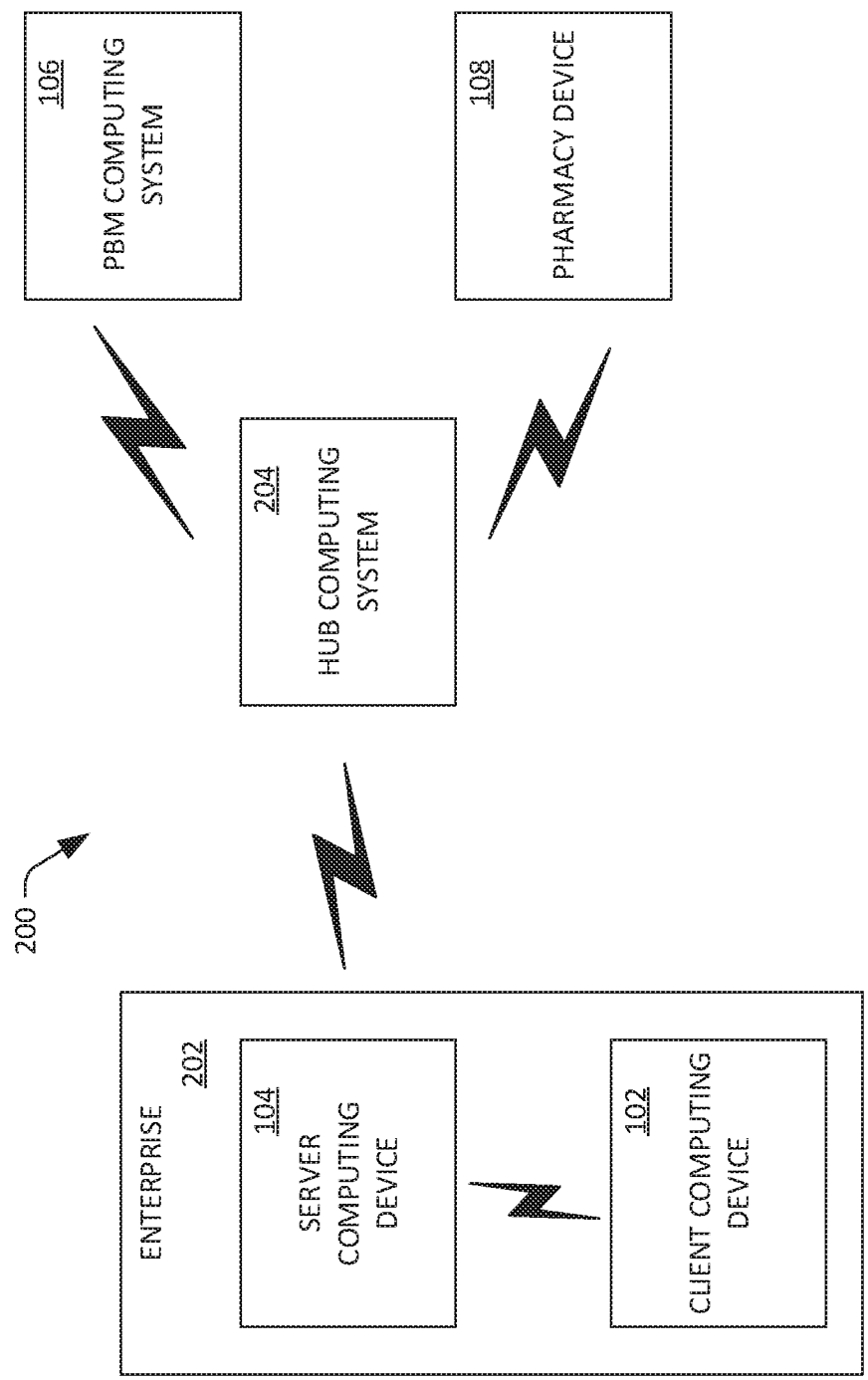
FIG. 2 is another functional block diagram of an exemplary computing system that facilitates automatically generating and transmitting a prescription.

Turning now to FIG. 2, a schematic of another exemplary computing system 200 that facilitates constructing and transmitting a prescription to a pharmacy device is illustrated. The system 200 includes the server computing device 104 (which executes the EHR 114) and the client computing device 102 (which executes the client application 122). In this example, the server computing device 104 and the client computing device 102 are both operated by an enterprise 202, such as a hospital, urgent care facility, or the like. The system 200 also includes the PBM computing system 106 and the pharmacy device 108, which operate as described above. In this example, the system 200 includes a hub computing system 204, which acts as an interface between the server computing device 104, the PBM computing system 106, and the pharmacy device 108. Further, while not shown, the hub computing system 204 may interface multiple server computing devices that execute multiple EHRs with multiple PBM computing systems and multiple pharmacy devices.

The hub computing system 204 may be referred to as a transaction hub. The hub computing system 204 can maintain a master patient index, a list of pharmacies, and a list of PBMs. Thus, the hub computing system 204 is configured to route messages between EHRs, PBM computing systems, and pharmacy devices. In an example, when the hub computing system 204 receives an approval request transmitted from the server computing device 104, the hub computing system 204 can verify the patient identified in the approval request with the master patient index and can route the approval request to the appropriate PBM computing system 106. As indicated previously, the PBM computing system 106, in response, can transmit information pertaining to patient eligibility, formulary, and medication history, to the hub computing system 204, which routes such response to the server computing device 104 (which in turn provides at least some of this information to the client computing device 102 for review by the clinician). It is to be understood that some computing architectures include a hub computing system, while others (such as shown in FIG. 1) need not include a hub computing system. These and other similar architectures are contemplated by the inventors and are intended to fall under the scope of the hereto appended claims.

Figure 3:
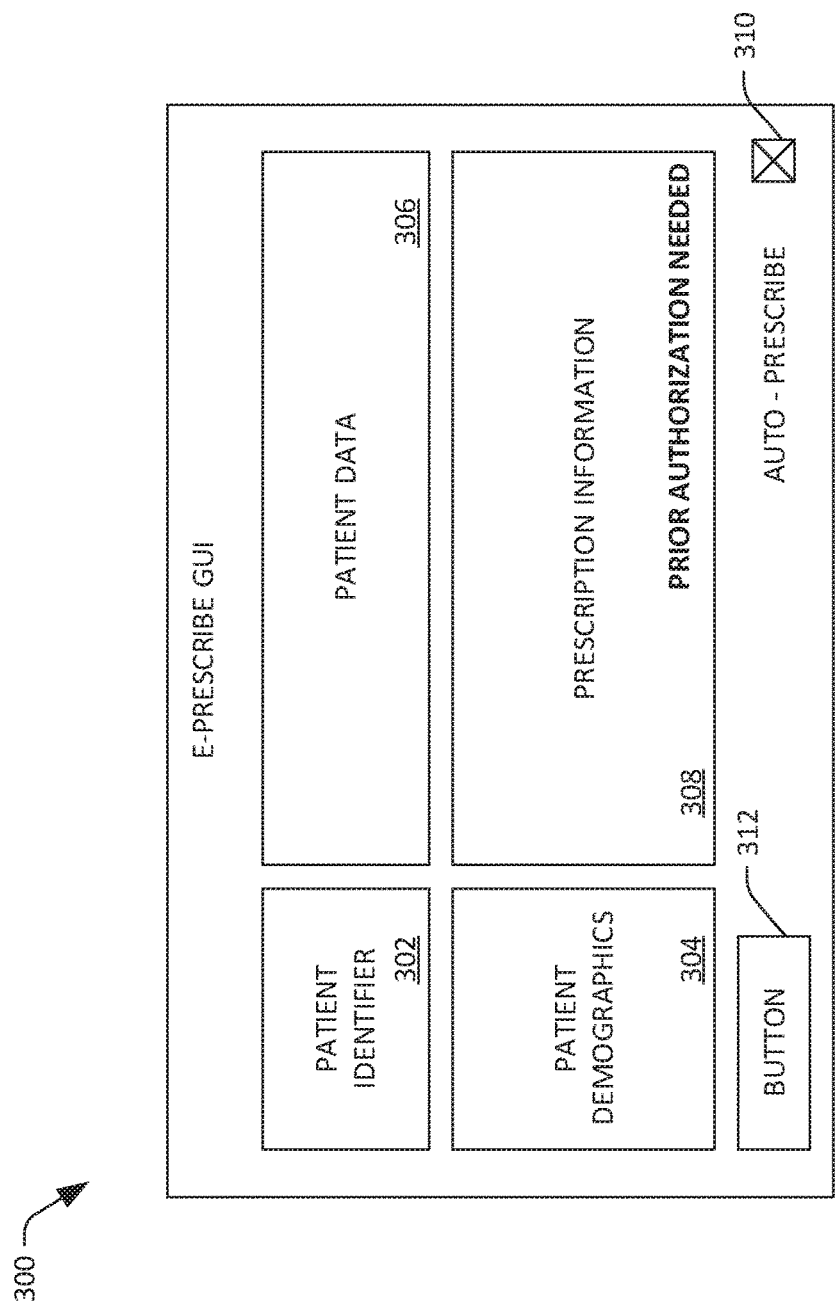
FIG. 3 is a schematic of an exemplary graphical user interface.

With reference now to FIG. 3, an exemplary GUI 300 that can be presented on the display 124 of the client computing device 102 when the client computing device 102 is operated by the clinician is illustrated. The GUI 300 includes a patient identifier 302, which can identify the patient who is being provided care by the clinician. The patient identifier 302, for instance, may be or include a name of the patient, an image of the patient, or some other information pertaining to the identity of the patient. The graphical user interface 300 may also include a patient demographics field 304 that depicts patient demographics, such as age of the patient, gender of the patient, ethnicity of the patient, and so forth. The graphical user interface 300 may also include a patient data field 306, where patient data can be presented. This patient data may include medications currently prescribed to the patient, medications prescribed to the patient in the past, historical treatment provided to the patient, and so forth.

The graphical user interface 300 may further include a field 308 that may be interacted with by the clinician in connection with indicating a desire to prescribe medication and/or treatment to the patient identified by the patient identifier 302. For instance, the prescription field 308 may include a list of medications that may be prescribed to the patient by the clinician, wherein each medication is selectable in the list. The field 308 can further include information that indicates that pre-approval from the PBM is needed for the clinician prescribing the medication to the patient. The field 308 can further include information, such as the identity of the pharmacy that is to fill the prescription, the communication modality that is to be used to present the prescription to the pharmacy, the prescription itself, including the identity of the medication and/or treatment, an identity of whether the prescription is refillable, an amount the dosage, etc.

The graphical user interface 300 also includes a checkbox 310 (e.g., the input element 128) that is shown in FIG. 3 as being selected by the clinician. This checkbox, when selected, indicates to the EHR 114 that the EHR 114 is to automatically construct a prescription for the medication and transmit the prescription to the pharmacy device 108 in response to the EHR receiving an approval message from the PBM computing system 106. The graphical user interface 300 may also include a button 312 that, when selected by the clinician, causes the information set forth by the clinician in the GUI 300 to be transmitted by the client computing device 102 to the server computing device 104 (including an indication that the checkbox 310 was selected). While shown as a checkbox 310, it is to be understood that the input element 128 may be a radio button, a text entry field, or some other input mechanism. While the GUI 300 indicates that the EHR provides an option for the EHR to automatically construct the prescription and transmit the prescription to the pharmacy device 108 for an individual request (e.g., for a certain patient and a certain prescription), it is to be understood that the EHR can provide an option for the EHR to automatically construct and transmit prescriptions at higher levels; for example, the EHR can provide an option that causes the EHR to automatically construct and transmit all prescriptions for the clinician, all prescriptions for a particular patient, all prescriptions for a certain subset of patients, all prescriptions for a certain medication, and so forth. Still further, the EHR can be provided with functionality such that the clinician can turn on (or off) the auto-prescribe feature after the request has been transmitted to the PBM but prior to receipt of the approval message from the PBM.

Figure 4:
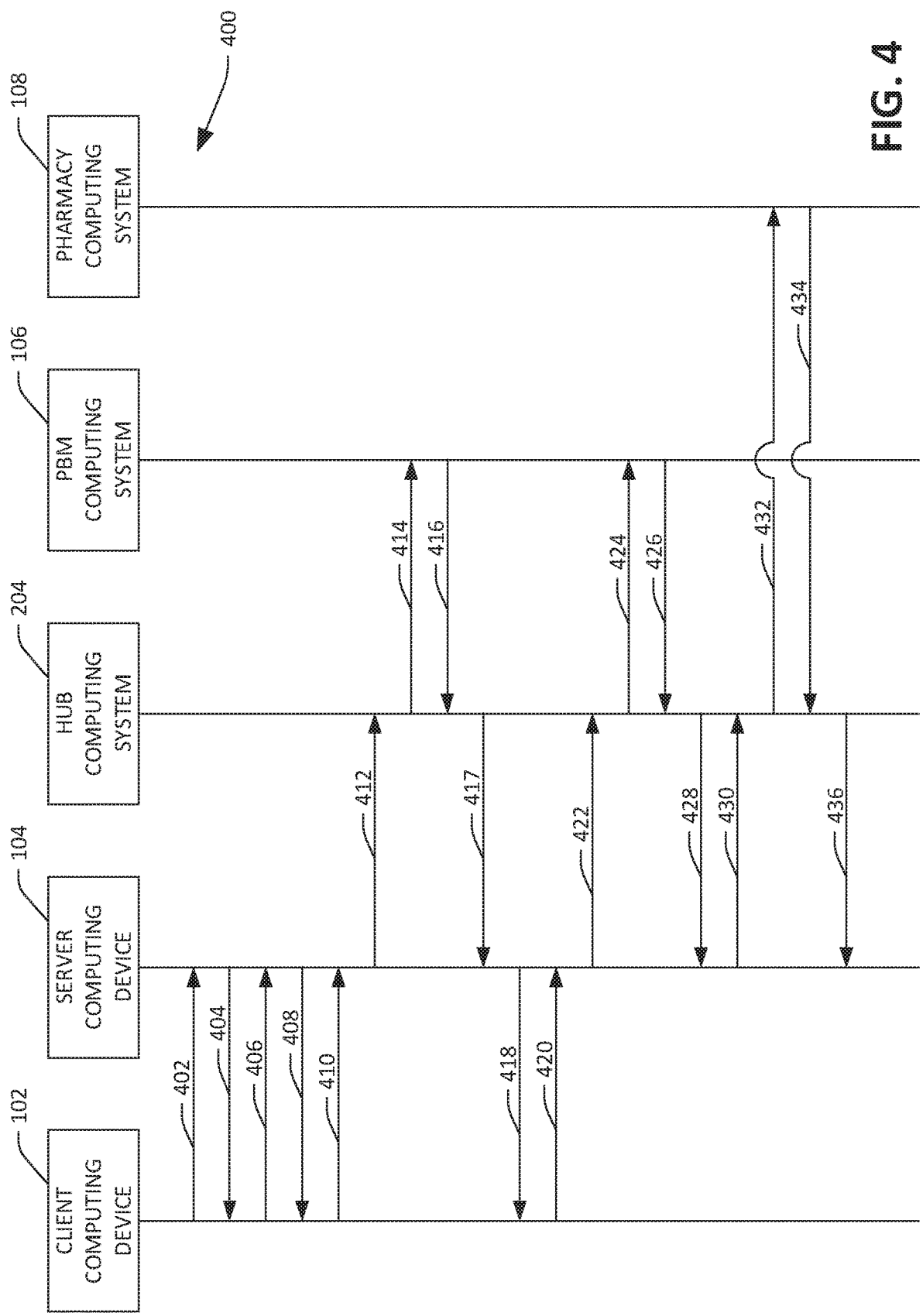
FIG. 4 illustrates a communications diagram.

Now referring to FIG. 4, an exemplary control flow diagram 400 is illustrated. At 402, the client computing device 102 transmits authentication data (set forth by the clinician) to the server computing device 104, wherein the EHR 114 executing on the server computing device 104 authenticates the clinician based upon the authentication data. At 404, he EHR 114 may cause data, customized for the clinician, to be transmitted for display on the display 124 of the client computing device 102. At 406, the client computing device 102, in response to input from the clinician, transmits a patient identifier to the server computing device 104. The server computing device 104 performs a search over the patient data 134 and locates data for the patient and/or the clinician. At 408, the server computing device 104 transmits at least a portion of the identified patient and/or clinician data to the client computing device 102.

The client computing device 102 receives input data from the clinician pertaining to a medication and/or treatment that is to be prescribed to the patient (referred to as prescription data). At 410, prescription data is transmitted to the server computing device 104, where the prescription data can include an identifier of the clinician, an identifier of the patient, a medication and/or treatment to be prescribed, an identifier of the pharmacy where the prescription is to be filled, a mode of communications to be used when transmitting the prescription to the pharmacy, dosage information, refill information, and so forth. The server computing device 104, in response to receipt of the prescription data, stores at least a portion of the prescription data in the data store 116 (as the input data 130). The server computing device 104 then constructs an approval request. The approval request can identify the patient, the medication and/or treatment, and optionally, the PBM corresponding to the patient. At 412, the server computing device 104 transmits the approval request to the hub computing system 204. At 414, the hub computing system 204 routes the approval request to the PBM computing system 106 based upon the identifier of the patient included in the approval request. In an exemplary embodiment, the hub computing system 204 identifies the PBM computing system 106 based upon the identifier of the patient, and optionally, the identifier of the medication in the approval request. In another embodiment, the PBM computing system 106 is identified directly in the approval request.

An employee of the PBM can review the approval request and set forth a request for additional information. At 416, the PBM computing system 106 can transmit a request for information to the hub computing system 204. As indicated previously, the approval request may include a unique reference number, and that reference number may be included in each message that is to be transmitted between the PBM computing system 106 and the server computing device 104 with respect to the requested prescription. In such an example, the hub computing system 204 can route the information request to the server computing device 104 based upon the reference number. In another example, the request for information may explicitly identify the server computing device 104. In yet another example, the hub computing system 204 can determine that the request for information is to be transmitted to the server computing device 104 based upon an identity of the clinician in the request for information, an identity of the patient in the request for information, and so forth.

At 417, the server computing device 104 transmits the request for information to the client computing device 102, and at 418 the request is transmitted from the server computing device 104 to the client computing device 102 operated by the clinician. The client computing device 102 can receive input from the clinician pertaining to a response to the information request, and at 420 the client computing device 102 can transmit this response information to the server computing device 104. In turn, at 422, the server computing device 104 can transmit the response to the hub computing system 204, which at 424 routes the response to the PBM computing system 106.

The PBM employee can review the response and, in an example, can approve the approval request. The PBM computing system 106 can receive input from the PBM employee that indicates that the approval request has been approved, causing the PBM computing system 106, at 426, to transmit an approval message to the hub computing system 204. At 428, the hub computing system 204 routes the approval message to the server computing device 104. As described previously, the EHR 114 is provided with the approval message and determines that the approval message is an approval for the previously transmitted approval request. Then, without receiving additional input from the clinician operating the client computing device 102, the server computing device 104 constructs a prescription and at 430 transmits the prescription to the hub computing system 204. At 432, the hub computing system 204 routes the prescription to the pharmacy device 108, where the prescription can be filled. Optionally, at 434, the pharmacy device 108 can be configured to generate a confirmation message, which is transmitted to the hub computing system 204. At 436, the hub computing system 204 routes the confirmation to the server computing device 104. The EHR 114 can, thus, receive confirmation that the pharmacy device 108 has received the automatically constructed prescription.

Figure 5:
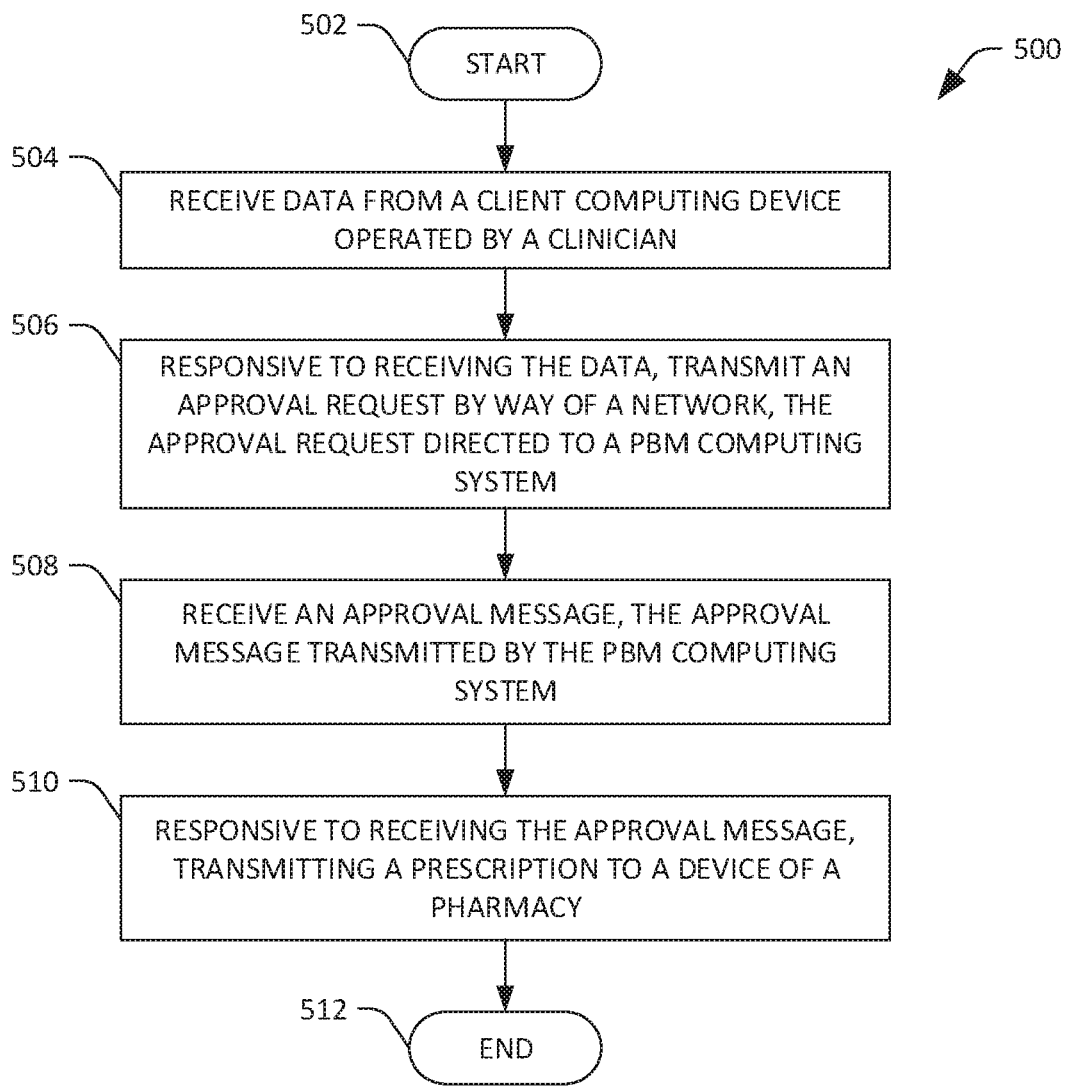
FIG. 5 is a flow diagram illustrating an exemplary methodology for generating and transmitting a prescription to a device of a pharmacy.
Figure 6:
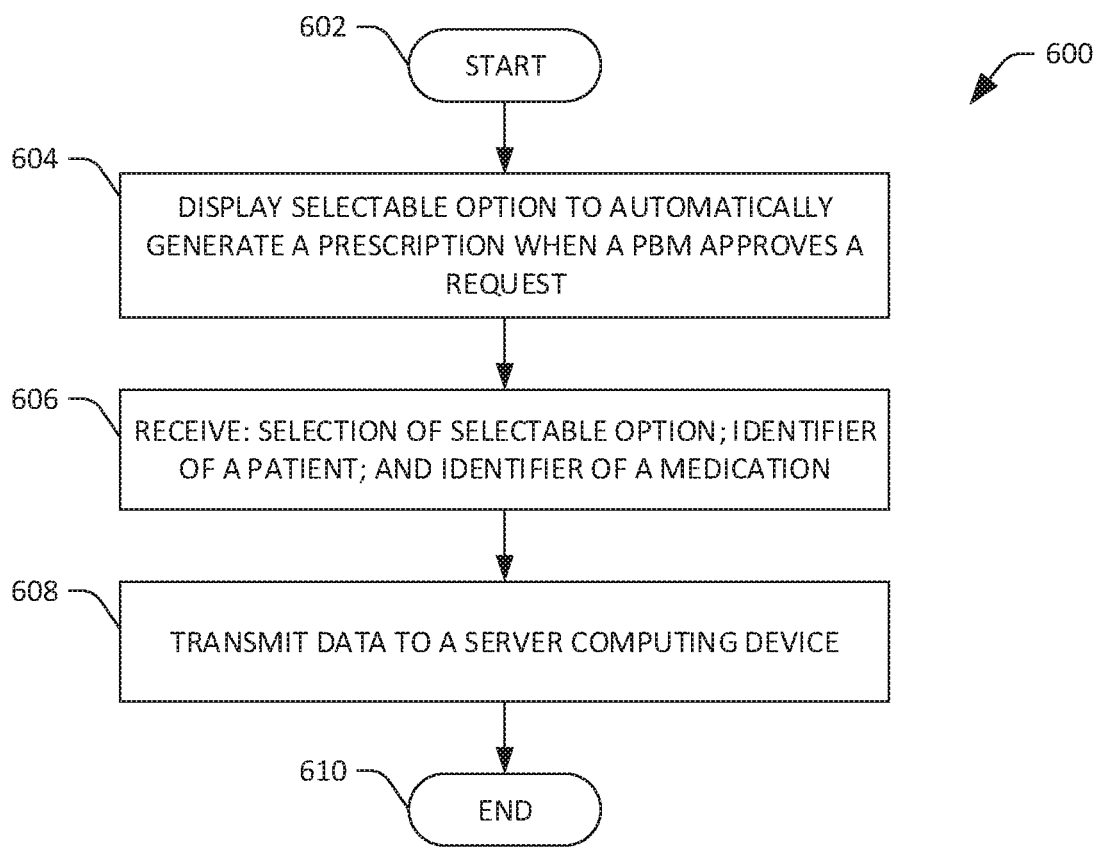
FIG. 6 is a flow diagram that illustrates an exemplary methodology for transmitting data from a client computing device to a server computing device that executes an EHR.

FIGS. 5-6 illustrate exemplary methodologies relating to an EHR automatically constructing and transmitting a prescription. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Now referring to FIG. 5, an exemplary methodology 500 for constructing and transmitting a prescription is illustrated, wherein the methodology 500 is performed by a server computing device that is executing an EHR. The methodology 500 starts at 502, and at 504, at the server computing device, data is received from a client computing device that is operated by a clinician. This data can include an identifier of the clinician, an identifier of a patient, an identifier of a medication that the clinician wishes to prescribe to the patient, an identifier of a pharmacy that is to fill the prescription, and an identifier of a communication modality to employ when transmitting the prescription to the pharmacy.

At 506, responsive to receiving the data, an approval request is transmitted by way of a network, wherein the approval request is directed to a PBM computing system. As indicated previously, this approval request can include a unique reference number corresponding to the approval request, an identifier of the patient, an identifier of the clinician, an identifier the medication dosage information, and so forth.

At 508, an approval message is received, wherein the approval message was transmitted by the PBM computing system and directed towards the server computing device. For instance, the approval message can include the unique reference number and may also include an authorization code. Thus, the EHR executing on the server computing device can ascertain that the approval message corresponds to the approval request and can further determine that the approval message approves the request. At 510, in response to receiving the approval message, a prescription is constructed and transmitted to a device of the pharmacy identified in the data received at 504. The methodology 500 completes at 512.

Now referring to FIG. 6, an exemplary methodology 600 that can be executed on a client computing device operated by a clinician is illustrated. The methodology 600 starts at 602, and at 604, on a display screen of the client computing device, a selectable option is displayed that, when selected, causes a prescription to be automatically constructed and transmitted to a PBM computing system when the PBM approves a request to prescribe medication and/or treatment to a patient. At 606, a selection of the selectable option is received from the clinician, an identifier of the patient is received from the clinician, and an identifier of the medication is received from the clinician. At 608, data is transmitted to a server computing device that is in communication with the client computing device, wherein the data includes an indication that the clinician has selected the selectable option, an identifier of the patient, and an identifier of the medication that is to be prescribed the patient. The methodology 600 completes at 610.

Figure 7:
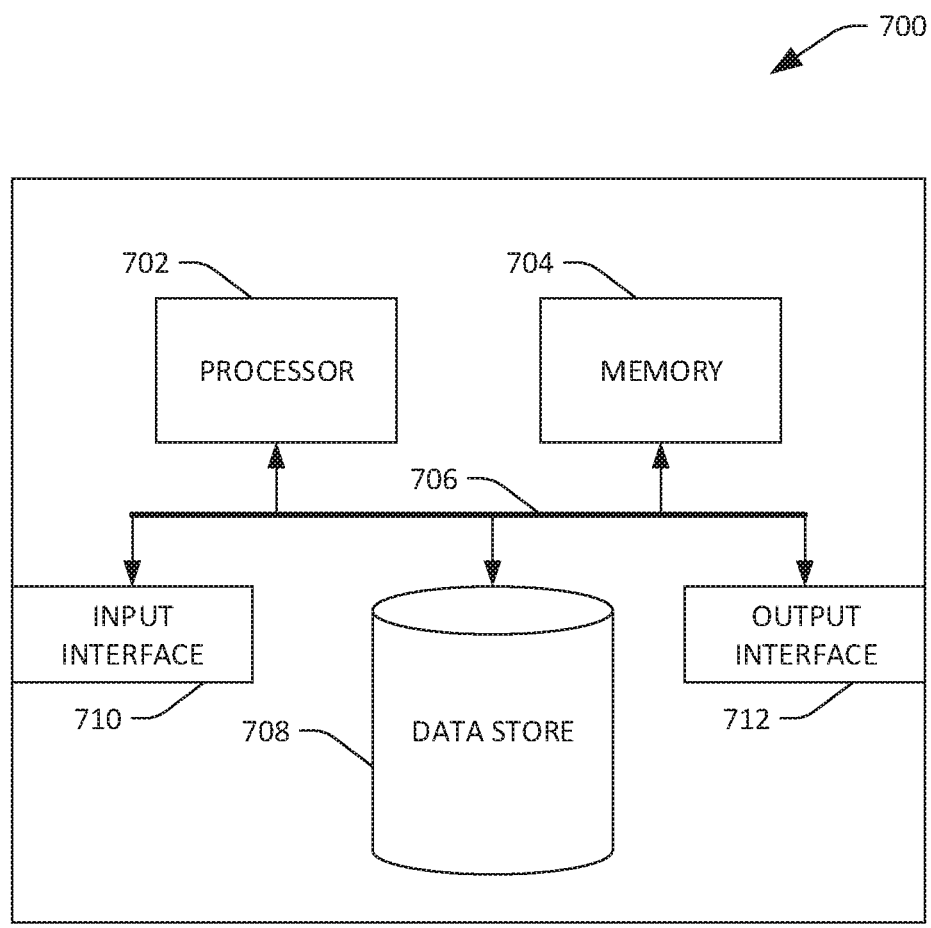
FIG. 7 is a schematic of an exemplary computing system.

Referring now to FIG. 7, a high-level illustration of an exemplary computing device 700 that can be used in accordance with the systems and methodologies disclosed herein is illustrated. For instance, the computing device 700 may be used in a system that executes an EHR. By way of another example, the computing device 700 can be used in a system that receives input from a clinician. The computing device 700 includes at least one processor 702 that executes instructions that are stored in a memory 704. The instructions may be, for instance, instructions for implementing functionality described as being carried out by one or more components discussed above or instructions for implementing one or more of the methods described above. The processor 702 may access the memory 704 by way of a system bus 706. In addition to storing executable instructions, the memory 704 may also store prescription-related data, patient information, etc.

The computing device 700 additionally includes a data store 708 that is accessible by the processor 702 by way of the system bus 706. The data store 708 may include executable instructions, images, patient data, etc. The computing device 700 also includes an input interface 710 that allows external devices to communicate with the computing device 700. For instance, the input interface 710 may be used to receive instructions from an external computer device, from a user, etc. The computing device 700 also includes an output interface 712 that interfaces the computing device 700 with one or more external devices. For example, the computing device 700 may display text, images, etc. by way of the output interface 712.

It is contemplated that the external devices that communicate with the computing device 700 via the input interface 710 and the output interface 712 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 700 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 700 may be a distributed system. Thus, for instance, several devices may be in communication by way of a network connection and may collectively perform tasks described as being performed by the computing device 700.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A server computing device comprising:
   at least one processor; and
   memory that has an electronic health record application (EHR) loaded therein, wherein the EHR, when executed by the at least one processor, causes the at least one processor to perform acts comprising:
   receiving, from a client computing device operated by a clinician, data that comprises:
      an indication that the clinician is requesting approval, from a pharmacy benefits manager (PBM), to prescribe a medication to a patient; and
      an indication that the prescription is to be automatically constructed and transmitted to a device of a pharmacy responsive to receipt of an approval message from the PBM;

responsive to receiving the data, causing an approval request to be transmitted to a computing system of the PBM by way of a network, the approval request comprises:
an identifier for the patient; and
an identifier for the medication that is to be prescribed by the clinician to the patient;
subsequent to transmitting the approval request, receiving at the EHR the approval message transmitted by the computing system of the PBM by way of the network, the approval message from the PBM authorizes a prescription for the medication for the patient to be provided to a pharmacy to fill the prescription; and
responsive to the EHR receiving the approval message, and without receipt of further input from the client computing device operated by the clinician, constructing by the EHR and without further input from the client computing device operated by the clinician the prescription; and
responsive to constructing the prescription, and without further input from the client computing device operated by the clinician, causing the prescription to be transmitted to a device managed by the pharmacy.

2. The server computing device of claim 1, wherein the data received from the client computing device further comprises:
an identity of the pharmacy where the prescription is to be transmitted; and
an identity of a mode of communication to be used to transmit the prescription to the pharmacy, the acts further comprising:
storing the data received from the client computing device in a database, wherein causing the prescription to be constructed comprises:
constructing the prescription based upon the data stored in the database.

3. The server computing device of claim 2, wherein constructing the prescription based upon the data stored in the database comprises:
identifying a form based upon the identity of the pharmacy; and
populating the form with an identity of the patient and an identity of the medication.

4. The server computing device of claim 1, the acts further comprising:
prior to causing the approval request to be transmitted to the computing system of the PBM, receiving an indication from the client computing device operated by the clinician that the EHR is to cause the prescription to be automatically transmitted to the device managed by the pharmacy in response to receipt of the approval message, wherein the prescription is transmitted to the device managed by the pharmacy only when the indication is received from the client computing device.

5. The server computing device of claim 1, the acts further comprising:
subsequent to causing the approval request to be transmitted and prior to receiving the approval message:
receiving an information request transmitted from the computing system of the PBM, the information request comprising a question for the clinician pertaining to at least one of the patient or the medication;
transmitting the question to the client computing device;
receiving, from the client computing device, an answer to the question provided by the clinician; and
responsive to receiving the answer to the question, causing a response to the information request to be transmitted to the computing system of the PBM, wherein the response to the information request comprises the answer to the question.

6. The server computing device of claim 1, wherein the approval message comprises an approval code, the acts further comprising:
identifying the approval code in the approval message;
including the approval code in the prescription; and
subsequent to including the approval code in the prescription, causing the prescription to be transmitted to the device managed by the pharmacy.

7. The server computing device of claim 1, wherein the device managed by the pharmacy is a facsimile machine.

8. The server computing device of claim 1, wherein causing the approval request to be transmitted to the computing system of the PBM by way of the network comprises:
transmitting the approval request to a hub computing device, wherein the approval request is routed by the hub computing device to the computing system of the PBM responsive to receiving the approval request, wherein the approval message transmitted by the computing system of the PBM by way of the network is received at the server computing device from the hub computing device.

9. The server computing device of claim 1, the acts further comprising:
authenticating the clinician based upon authentication data received from the client computing device;
transmitting health data about the patient to the client computing device responsive to authenticating the clinician; and
receiving, from the client computing device, an indication that the approval request is to be transmitted to the computing system of the PBM, wherein the indication includes a confirmation that the prescription is to be transmitted to the pharmacy immediately responsive to the server computing device receiving the approval message.

10. The server computing device of claim 9, wherein the indication further includes an identity of a communication modality to be employed when transmitting the prescription to the pharmacy.

11. A method performed by a server computing device when at least one processor of the server computing device executes an electronic health records (EHR) application, the method comprising:
receiving, from a client computing device operated by a clinician, data that comprises:
an indication that the clinician is requesting approval, from a pharmacy benefits manager (PBM), to prescribe a medication to a patient;
an identity of a pharmacy that is to fill a prescription for the medication for the patient; and
an indication that the prescription is to be automatically constructed and transmitted to a device of a pharmacy responsive to receipt of an approval message from the PBM;
responsive to receiving the data, transmitting an approval request by way of a network, the approval request directed to a PBM computing device, the approval request comprises:
an identifier for the patient; and
an identifier for the medication;
subsequent to transmitting the approval request, receiving at the EHR the approval message, the approval message transmitted by the PBM computing device, the approval message from the PBM comprises approval data that indicates that the PBM has approved prescribing of the medication to the patient;

responsive to receiving the approval message and based upon the approval data and the data received from the client computing device, constructing by the EHR and without further input from the client computing device operated by the clinician the prescription; and responsive to constructing the prescription, transmitting the prescription to the device of the pharmacy.

12. The method of claim 11, wherein the indication that the prescription is to be automatically transmitted to the device of the pharmacy is generated based upon the clinician selecting a radio button or check box in a graphical user interface presented on the client computing device operated by the clinician.

13. The method of claim 11, further comprising:
subsequent to transmitting the approval request, receiving a request for information from the PBM computing device;
transmitting the request for information to the client computing device operated by the clinician responsive to the clinician being authenticated by the EHR application at the server computing device;
receiving a response to the request for information from the client computing device operated by the clinician; and
responsive to receiving the response to the request for information, transmitting the response to the request for information, the response to the request for information directed to the PBM computing device.

14. The method of claim 13, wherein the response to the request for information includes an attached document, the attached document comprises information about at least one of the patient or the medication.

15. The method of claim 13, further comprising:
responsive to receiving the request for information from the PBM computing device, performing a search over health data stored at the server computing device based upon at least one of the identifier for the patient or the identifier for the medication;
identifying proposed response data to the request for information based upon the search; and
transmitting the proposed response data to the client computing device for approval by the clinician.

16. The method of claim 11, wherein transmitting the approval request by way of the network comprises transmitting the approval request to a hub computing system, the hub computing system is configured to route the approval request to the PBM computing device.

17. The method of claim 11, wherein constructing the prescription comprises populating a form based upon the data received from the client computing device.

18. The method of claim 17, wherein constructing the prescription further comprises identifying the form based upon the identity of the pharmacy.

19. A server computing device comprising computer-readable storage media, the computer-readable storage media comprising an electronic health records application (EHR) that, when executed by at least one processor, causes the at least one processor to perform acts comprising:
receiving, from a client computing device operated by a clinician, data that comprises:
an indication that the clinician is requesting approval, from a pharmacy benefits manager (PBM), to prescribe a medication to a patient;
an identity of a pharmacy that is to fill a prescription for the medication for the patient; and
an indication that the prescription is to be automatically constructed and transmitted to a device of a pharmacy responsive to receipt of an approval message from the PBM;
responsive to receiving the data, transmitting an approval request by way of a network, the approval request directed to a PBM computing device, the approval request comprises:
an identifier for the patient; and
an identifier for the medication;
subsequent to transmitting the approval request, receiving at the EHR the approval message, the approval message transmitted by the PBM computing device, the approval message comprises approval data that indicates that the PBM has approved prescribing of the medication to the patient;
responsive to receiving the approval message, and without further input from the client computing device, constructing by the EHR and without further input from the client computing device operated by the clinician the prescription for the medication based upon the identifier for the patient and the identifier for the medication included in the approval request; and
responsive to constructing the prescription, transmitting the prescription to the device of the pharmacy.

20. The server computing device of claim 19, wherein the approval request further comprises:
an identifier for the pharmacy; and
a mode of communication that is to be employed when transmitting the prescription to the device of the pharmacy, wherein the prescription is constructed based upon the identifier for the pharmacy and the mode of communication included in the approval request.

* * * * *